United States Patent
Cosmescu

(10) Patent No.: US 12,201,341 B2
(45) Date of Patent: Jan. 21, 2025

(54) ULTRAPOLAR ELECTROSURGERY BLADE AND ULTRAPOLAR ELECTROSURGERY BLADE ASSEMBLY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 0 days.

(21) Appl. No.: 18/581,228

(22) Filed: Feb. 19, 2024

(65) Prior Publication Data

US 2024/0189011 A1    Jun. 13, 2024

Related U.S. Application Data

(63) Continuation of application No. 17/520,486, filed on Nov. 5, 2021, now Pat. No. 11,903,629, which is a (Continued)

(51) Int. Cl.
*A61B 18/04* (2006.01)
*A61B 18/00* (2006.01)
(Continued)

(52) U.S. Cl.
CPC .......... *A61B 18/04* (2013.01); *A61B 18/1477* (2013.01); *A61B 18/16* (2013.01); (Continued)

(58) Field of Classification Search
CPC .............. A61B 18/04; A61B 2018/126; A61B 2018/1412; A61B 2018/162; A61B 2018/00077; A61B 2018/00107; A61B 2018/00589; A61B 2018/00601; A61B 2018/00607; A61B 2018/1253; A61B 2018/1415; A61B 2018/1467; A61B 18/042; A61B 18/14; A61B 18/1477
See application file for complete search history.

(56) References Cited

U.S. PATENT DOCUMENTS 4,043,342 A   8/1977 Morrison, Jr.
4,202,337 A   5/1980 Hren et al.
(Continued)

FOREIGN PATENT DOCUMENTS

EP    0280798 A1    9/1988

*Primary Examiner* — Daniel W Fowler
*Assistant Examiner* — Bradford C. Blaise
(74) *Attorney, Agent, or Firm* — Zeman-Mullen & Ford, LLP

(57) ABSTRACT

An ultrapolar electrosurgery blade includes top and bottom thin elongated conductive members in vertical alignment and spaced apart from one another along their lengths, a non-conductive housing or coating covering both the top and bottom thin elongated conductive members and the space located between them to create opposing non-conductive sides of the blade with a non-conductive cutting end located between exposed conductive cutting ends, and both return and active contact layers located on each of the opposing non-conductive sides of the blade. An ultrapolar electrosurgery blade assembly having argon beam capability further includes a non-conductive tube member having a slot positioned over the top of the ultrapolar electrosurgery blade and a conductive hollow tubular member contained within at least a portion of the non-conductive tube member.

20 Claims, 10 Drawing Sheets

Related U.S. Application Data continuation of application No. 15/919,995, filed on Mar. 13, 2018, now Pat. No. 11,166,757.

(60) Provisional application No. 62/576,222, filed on Oct. 24, 2017, provisional application No. 62/470,400, filed on Mar. 13, 2017.

(51) Int. Cl.
  *A61B 18/14* (2006.01)
  *A61B 18/16* (2006.01)

(52) U.S. Cl.
  CPC .............. *A61B 2018/00077* (2013.01); *A61B 2018/00083* (2013.01); *A61B 2018/00607* (2013.01); *A61B 2018/1412* (2013.01); *A61B 2018/1467* (2013.01); *A61B 2018/162* (2013.01); *A61B 2218/008* (2013.01)

(56) References Cited

U.S. PATENT DOCUMENTS

| | | |
|---|---|---|
| 4,248,231 A | 2/1981 | Herczog et al. |
| 4,674,498 A | 6/1987 | Stasz |
| 4,850,353 A | 7/1989 | Stasz et al. |
| 5,281,216 A | 1/1994 | Klicek |
| 6,974,452 B1 | 12/2005 | Gille et al. |
| 7,211,084 B2 | 5/2007 | Goble et al. |
| 7,727,232 B1 | 6/2010 | Maurer et al. |
| 11,109,907 B2 | 9/2021 | Cosmescu |
| 11,166,757 B2 | 11/2021 | Cosmescu |
| 2006/0241588 A1 | 10/2006 | Heim et al. |
| 2010/0094283 A1 | 4/2010 | Cosmescu |
| 2013/0110108 A1 | 5/2013 | Davison et al. |
| 2013/0331657 A1 | 12/2013 | Basson et al. |
| 2014/0257273 A1 | 9/2014 | Cosmescu |
| 2016/0317209 A1 | 11/2016 | Cosmescu |
| 2017/0056054 A1 | 3/2017 | Dickerson et al. |
| 2017/0319255 A1 | 11/2017 | Cosmescu |
| 2018/0071011 A1 | 3/2018 | Cosmescu |

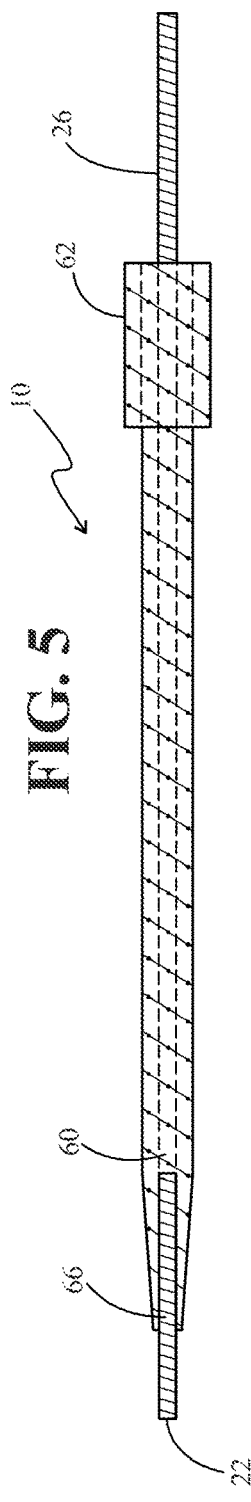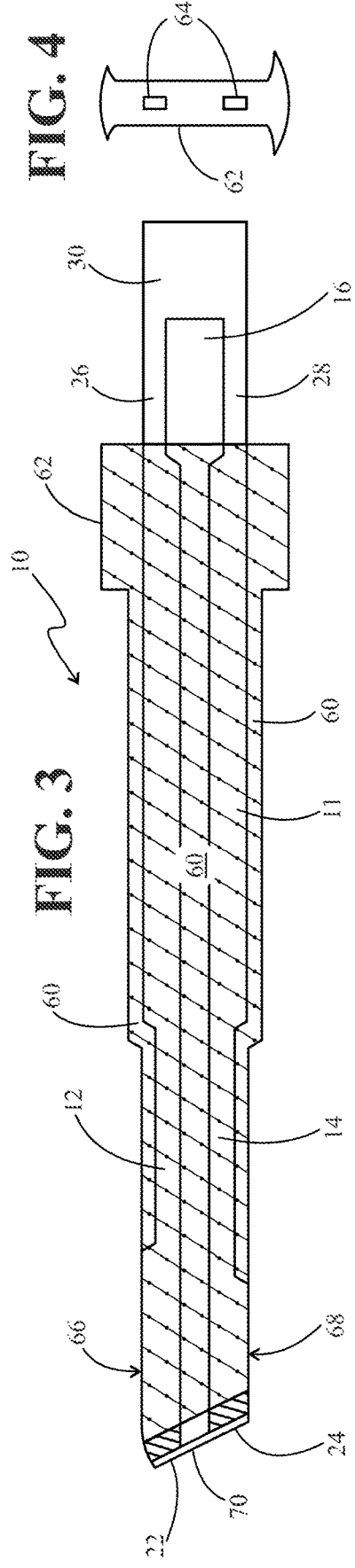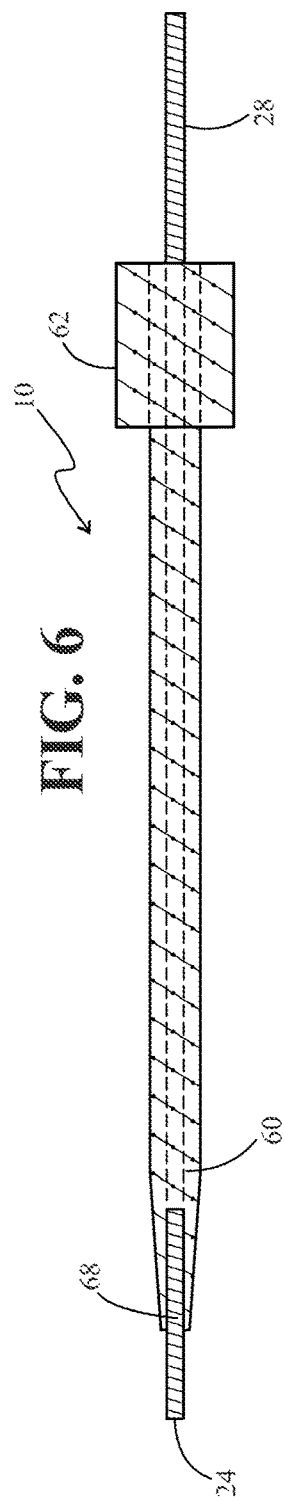

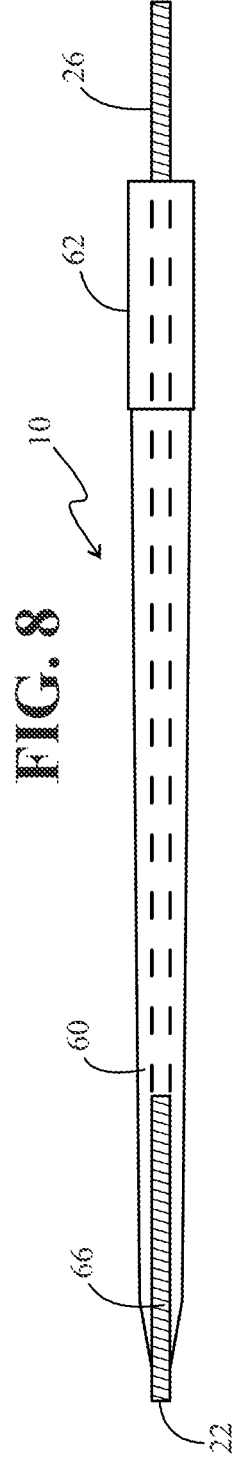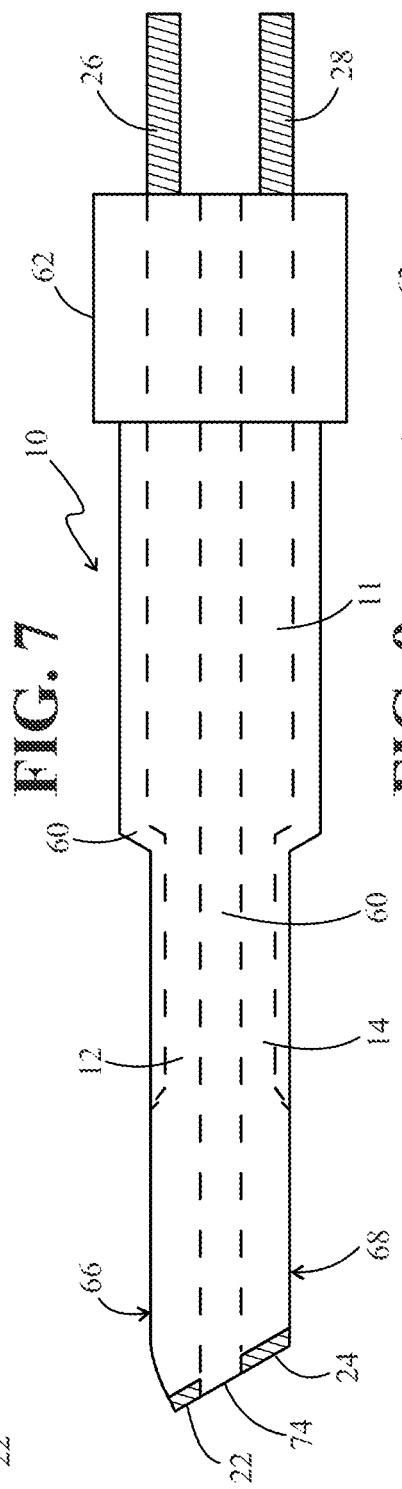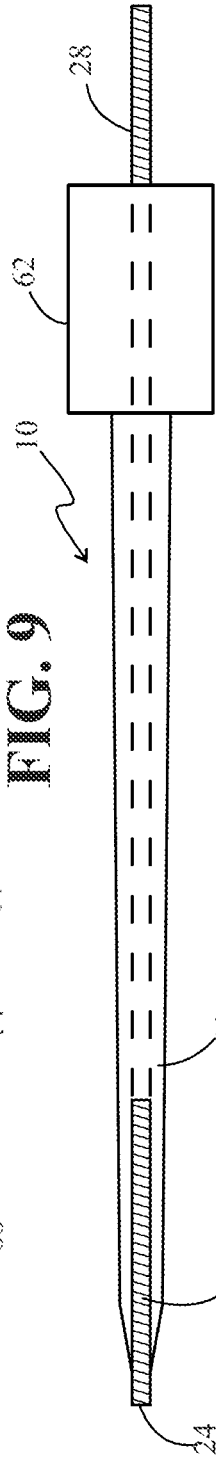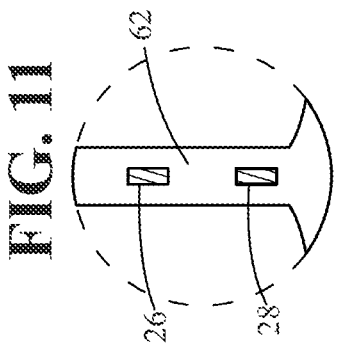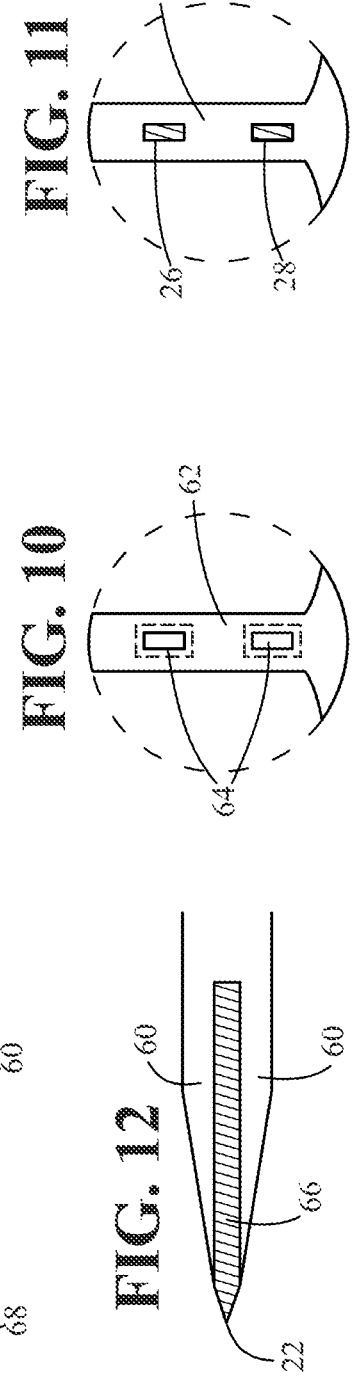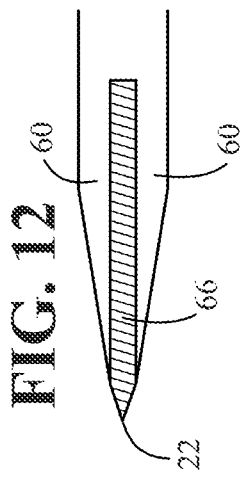

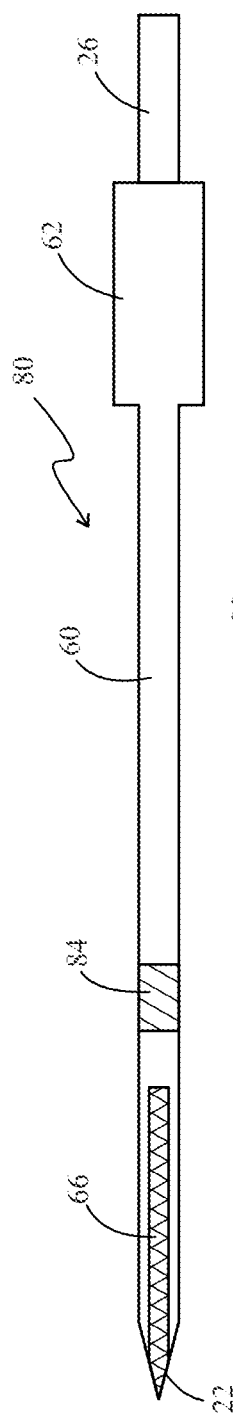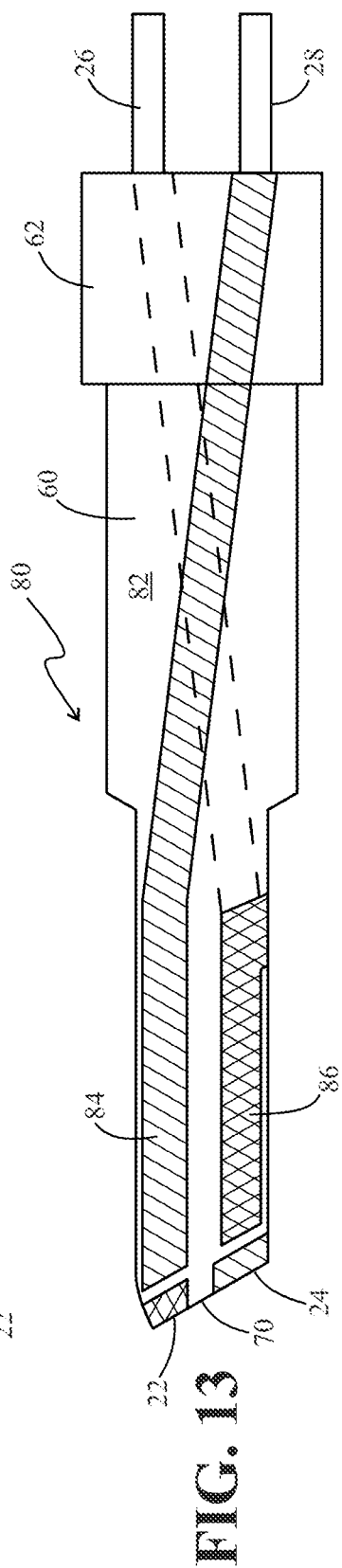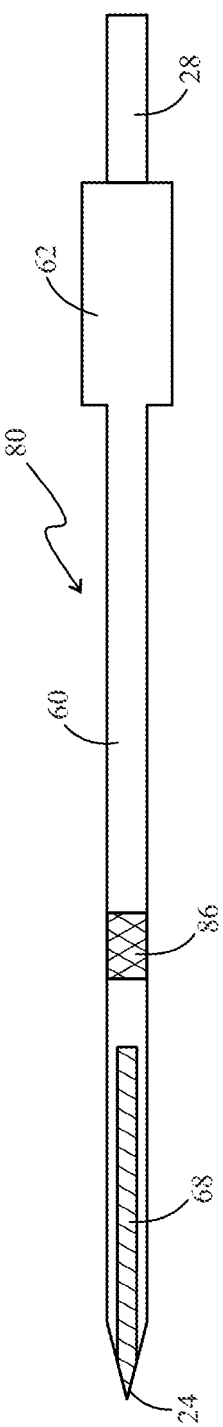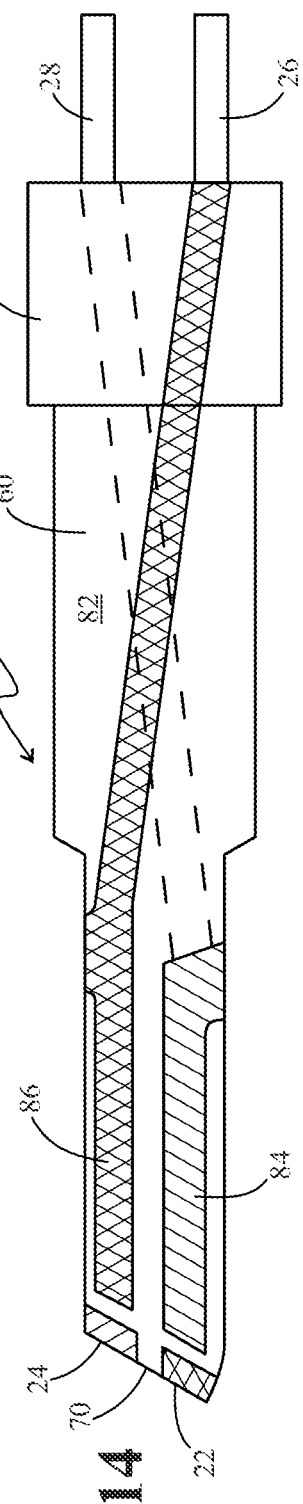
FIG. 15
FIG. 13
FIG. 16
FIG. 14

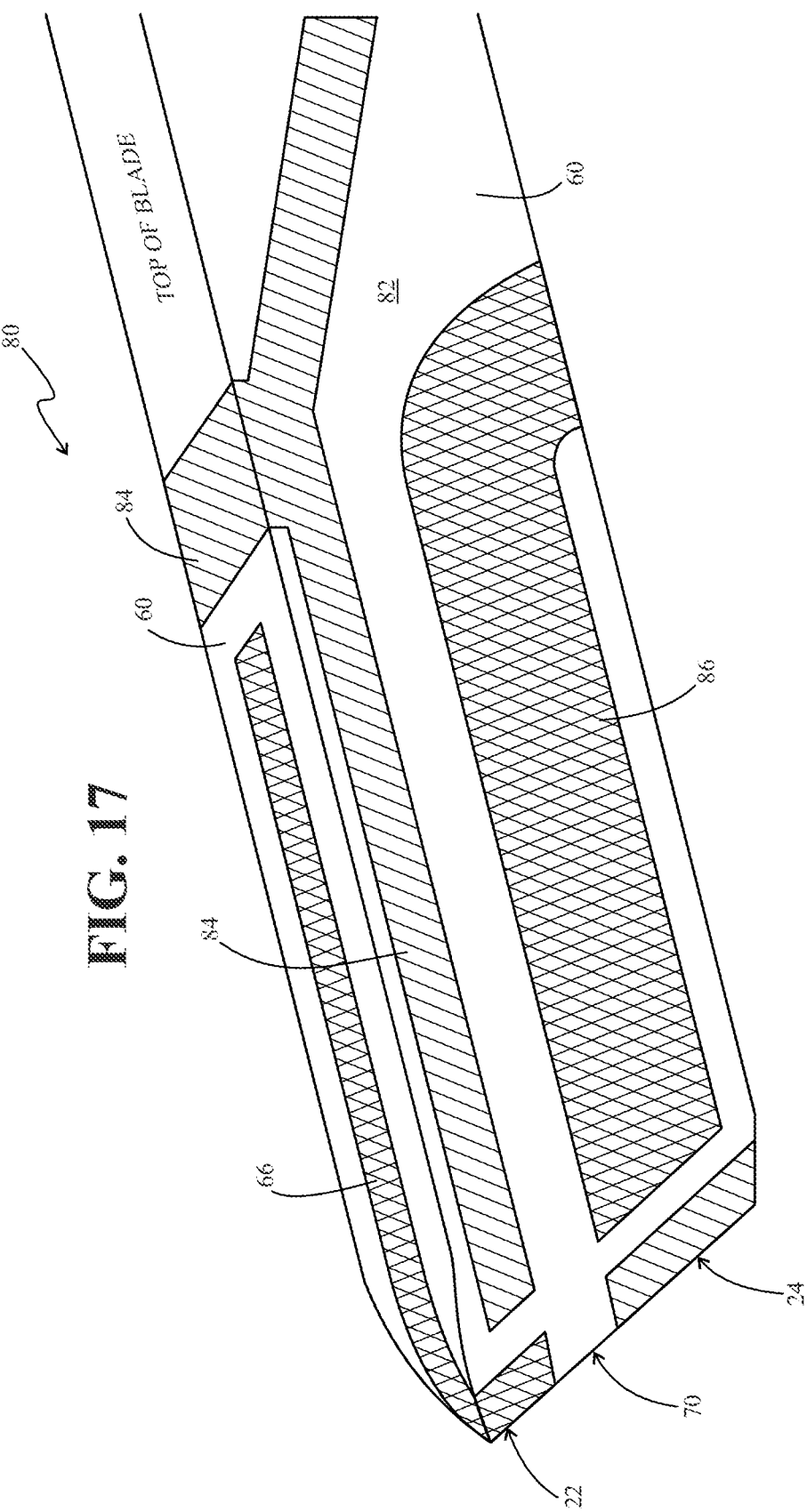

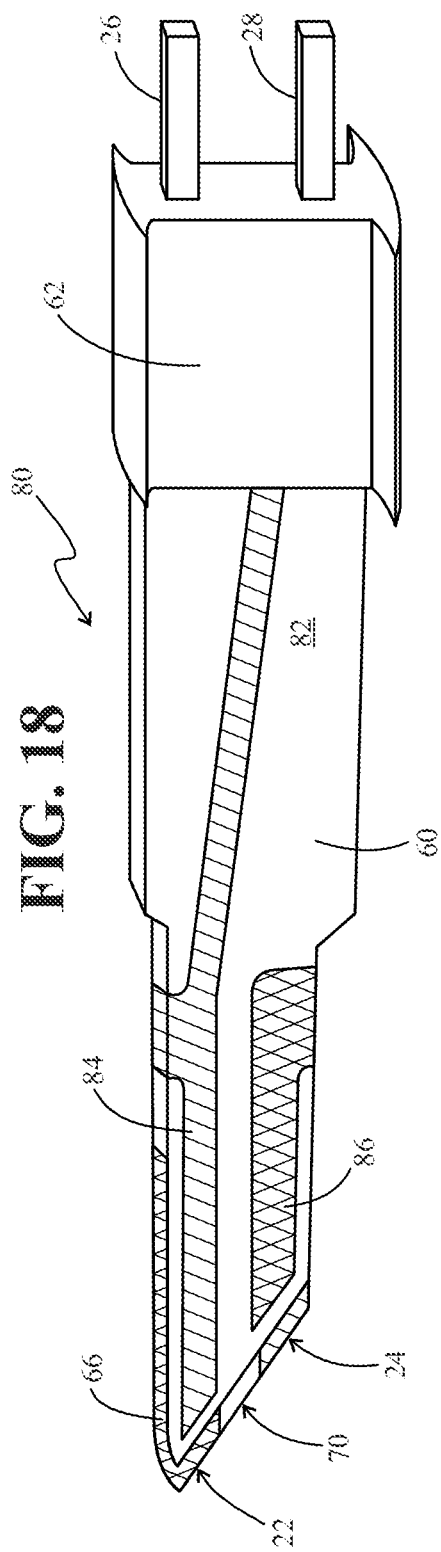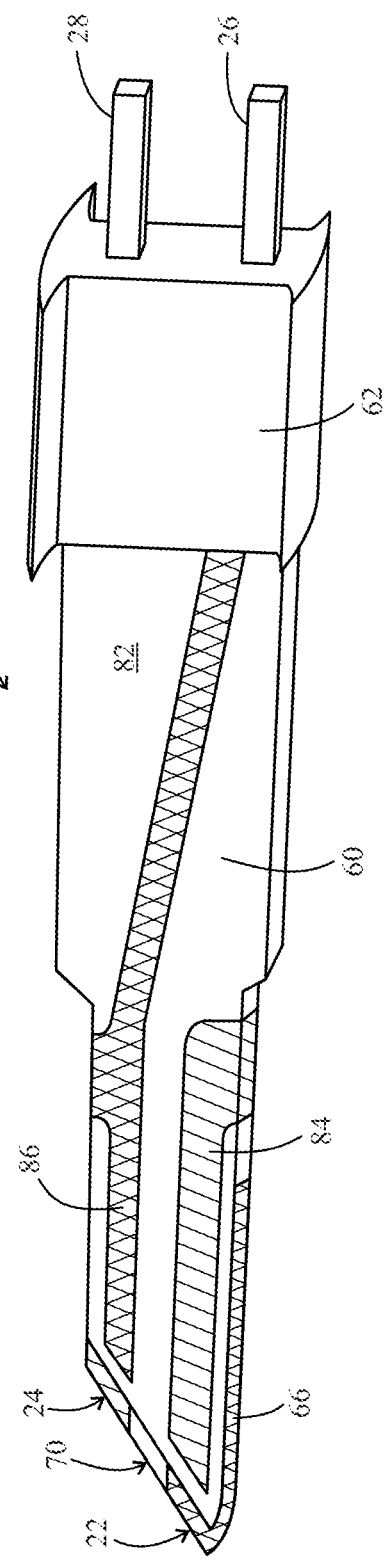

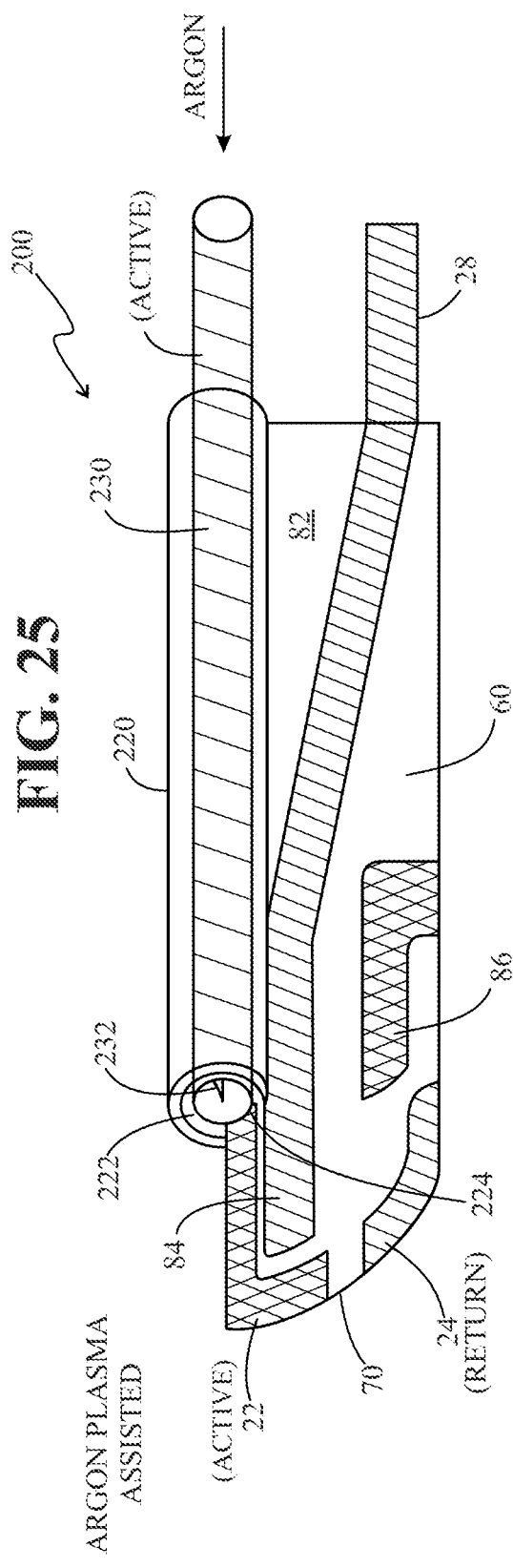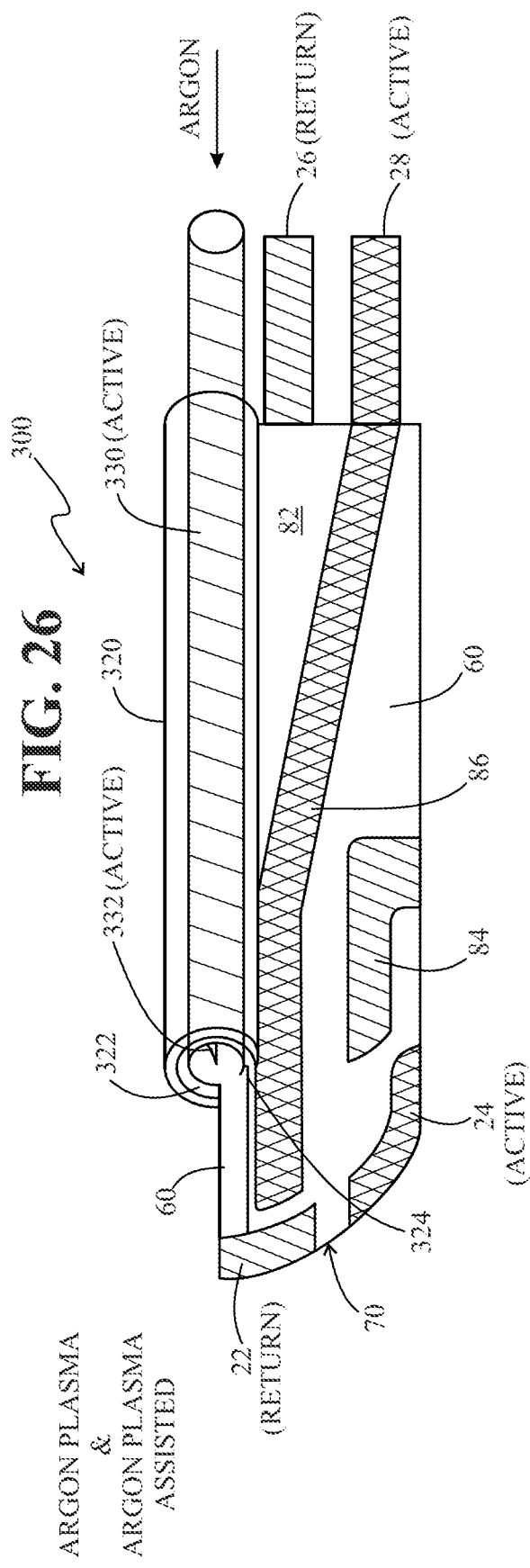

ULTRAPOLAR ELECTROSURGERY BLADE AND ULTRAPOLAR ELECTROSURGERY BLADE ASSEMBLY

CROSS-REFERENCE TO RELATED APPLICATIONS

This application relates to provisional patent applications having Ser. Nos. 62/467,739 and 62/576,213 and their related utility application having Ser. No. 15/913,569, filed on Mar. 6, 2018, and which issued as U.S. Pat. No. 11,109,907 on Sep. 7, 2021. Further, this application claims priority to utility patent application having Ser. No. 17/520,486, filed Nov. 5, 2021 (which issued as U.S. Pat. No. 11,903,629 on Feb. 20, 2024), which claims priority to U.S. Pat. No. 11,166,757, issued Nov. 9, 2021, which claims priority to provisional patent application having Ser. No. 62/470,400, filed Mar. 13, 2017, and provisional patent application having Ser. No. 62/576,222, filed Oct. 24, 2017, which are all herein incorporated by reference in their entireties.

FIELD OF INVENTION

The present invention is generally directed to an ultrapolar electrosurgery blade and an ultrapolar electrosurgery blade assembly which uses monopolar energy in a bipolar mode for cutting and coagulation. The ultrapolar electrosurgery blade is the same as that disclosed in provisional applications having Ser. No. 62/467,739 and Ser. No. 62/576,213 and their related utility patent application having Ser. No. 15/913,569 [which includes top and bottom thin elongated conductive members in vertical alignment with one another and spaced apart from one another along their lengths where each of the elongated conductive members (one of which functions as an active electrode while the other functions as a return electrode) includes opposing planar sides, a sharp cutting end, and an opposite non-cutting end, and a non-conductive coating covering both opposing sides of the top and bottom thin elongated conductive members and the space between them where at least a portion of the cutting ends of the top and bottom elongated conductive members and their opposite non-cutting ends remain exposed] but also further includes an active conductive layer and a return conductive layer on each side of the non-conductive coating that covers the top and bottom thin elongated conductive members. The return conductive layers on each side of the non-conductive coating may be joined by a return conductive layer that extends over a non-conductive top or bottom of the ultrapolar electrosurgery blade thereby providing a continuous return conductive layer that extends from one non-conductive coating side of the ultrapolar electrosurgery blade to the other non-conductive coating side of the ultrapolar electrosurgery blade. Similarly, the active conductive layers on each side of the non-conductive coating may be joined by an active conductive layer that extends over a non-conductive top or bottom of the ultrapolar electrosurgery blade thereby providing a continuous active conductive layer that extends from one non-conductive coating side of the ultrapolar electrosurgery blade to the other non-conductive coating side of the ultrapolar electrosurgery blade. The ultrapolar electrosurgery blade may further include a non-conductive support member/socket having two openings therein in vertical alignment with one another where a portion of the top and bottom thin elongated conductive members located near their non-cutting ends are respectively contained within one of the two openings of the support member/socket so that the ultrapolar electrosurgery blade of the present invention can be seated and retained within an electrosurgery pencil. The ultrapolar electrosurgery blade of the present invention is capable of cutting tissue with the sharp conductive cutting ends of the blade without using RF energy as well as cutting tissue with the sharp non-conductive cutting end/edge that is located between the sharp conductive cutting ends. In addition, the ultrapolar electrosurgery blade of the present invention is capable of coagulating tissue and/or enhanced cutting of tissue by supplying low power to the ultrapolar electrosurgery blade, and simultaneously cutting and coagulating tissue by cutting tissue with the sharp cutting ends of the ultrapolar electrosurgery blade while coagulating tissue by applying low power to the ultrapolar electrosurgery blade.

The present invention is also directed to an ultrapolar electrosurgery blade assembly with argon beam capability which includes the previously described ultrapolar electrosurgery blade, a non-conductive tube member having a hollow tubular shaped opening contained therein and a slot where the slot is positioned over the top of the ultrapolar electrosurgery blade, and a conductive hollow tubular member contained within at least a portion of the non-conductive tube member where the conductive hollow tubular member includes a conductive projection extending from an end of the conductive hollow tubular member contained within the non-conductive tube member. Argon gas that is supplied through the conductive hollow tubular member and into the non-conductive tube member is ionized and directed by the conductive projection of the conductive hollow tubular member. The non-conductive coating is a continuous coating that also fills any space located between the sharp cutting ends of the top and bottom thin elongated conductive members to create a sharp non-conductive cutting end of the ultrapolar electrosurgery blade located between the sharp conductive cutting ends of the top and bottom thin elongated conductive members. The conductive hollow tubular member contained within the non-conductive tube member may also include a slot that is positioned over a top portion of the ultrapolar electrosurgery blade. The ultrapolar electrosurgery blade assembly with argon beam capability provides argon plasma coagulation of tissue and/or argon plasma assisted cutting and/or argon plasma assisted coagulation of tissue depending on the location and configuration of the active and return electrodes and the active and return conductive contact layers of the ultrapolar electrosurgery blade.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monpolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the high power necessary to conduct monopolar electrosurgery and the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy and thereby reduces or eliminates the likelihood of tissue damage and sparking associated with monopolar electrosurgery, it has limited ability to cut and coagulate large bleeding areas.

Since surgical tools and devices currently available to surgeons require switching between cutting and coagulation modes during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade having a sharp edge for cutting and RF for coagulation would meet this need. The ultrapolar electrosurgery blade of the present invention which uses monopolar energy in a bipolar mode has sharp cutting edges made of a hard conductive material, such as stainless steel, tungsten, etc. that are separated by a sharp non-conductive cutting edge that can all be used for precisely cutting tissue without the use of any RF energy. However, RF energy can also be used with the ultrapolar electrosurgery blade of the present invention for coagulation. When low voltage is used to supply power to the ultrapolar electrosurgery blade of the present invention for coagulation, the sharp cutting edges of the ultrapolar electrosurgery blade can simultaneously be used for cutting without the need to provide higher voltage to the ultrapolar electrosurgery blade to carry out the cutting. Therefore, there is no need to switch over to a cutting mode to perform cutting and instead both cutting and coagulation can be performed simultaneously at low power levels supplied from the generator.

There is also a need for a surgical tool or device that enables a surgeon or user to use low power monopolar energy in a bipolar mode while performing electrosurgery to avoid or eliminate current diversion, to reduce or eliminate lateral damage to the patient's tissue, and to increase accuracy and efficiency of the surgery and decrease operating time. The low power used to employ the ultrapolar electrosurgery blade of the present invention for both cutting and coagulation substantially reduces the damage to the lateral tissue and the tissue will not stick to the ultrapolar blade. Further, since the ultrapolar electrosurgery blade of the present invention includes top and bottom conductive members/electrodes, as well as active and return conductive contact layers, that are all attached to the generator, only a very small amount of a patient's tissue located between the electrodes or conductive contact layers, or adjacent to the electrodes or conductive contact layers, is included in the circuit thereby eliminating the risk of current diversion to other parts of the patient that can occur in monopolar systems where the entire patient is in the circuit.

It is also common to use argon beam coagulators during electrosurgery. In argon beam coagulation (ABC), plasma is applied to tissue by a directed beam of ionized argon gas (plasma) which causes a uniform and shallow coagulation surface thereby stopping blood loss. In some instances, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as making incisions in tissue by cutting, or stopping the bleeding at the surgical site. Therefore, there is also a need for a surgical device or tool that enables a surgeon or user to perform electrosurgery with an electrosurgery blade and coagulate tissue using argon beam coagulation at the surgical site at the same time, or simultaneously, without the need to switch between argon beam coagulation and electrosurgery modes. Further still, there is also a need for an electrosurgical device that enables a user or surgeon to choose from a number of different separate or combined tissue cutting and coagulation methods since different methods may work best depending on the surgical procedure and circumstances that present themselves during surgery.

The ultrapolar electrosurgery blade assembly with argon beam capability of the present invention is capable of coagulating a patient's tissue using argon plasma alone without contacting the patient's tissue (i.e. non-contact argon beam coagulation). In this embodiment of the ultrapolar electrosurgery blade assembly, an exposed portion of the return electrode of the ultrapolar electrosurgery blade is positioned near the top of the electrosurgery blade such that it is in alignment with the conductive hollow tubular member through which the argon gas is introduced and the conductive projection extending from an end of the conductive tube member so that a complete circuit is formed to ionize the argon gas for argon plasma coagulation. The ultrapolar electrosurgery blade assembly of the present invention is also capable of cutting a patient's tissue using the sharp cutting edge (comprising both conductive and non-conductive materials) of the ultrapolar blade alone without any use of RF energy and without any use of argon plasma. The ultrapolar electrosurgery blade assembly of the present invention can also enhance the cutting of a patient's tissue using the sharp conductive cutting edges of the ultrapolar blade by also supplying RF energy to the ultrapolar electrosurgery blade. Moreover, the ultrapolar electrosurgery blade assembly of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar blade can be used without any RF energy for cutting while the conductive tube through which the argon gas is introduced, and which is contained within the non-conductive tube, is activated and directed to provide ionized argon gas for argon plasma coagulation of tissue. In another example, low power may be applied to the ultrapolar blade to coagulate tissue or enhance cutting of tissue while the conductive tube through which the argon gas is introduced, and which is contained within the non-conductive tube, is activated and directed to provide ionized argon gas for argon plasma coagulation of tissue.

Both the ultrapolar electrosurgery blade of the present invention and the ultrapolar electrosurgery blade assembly having argon beam capability of the present invention could be used with an electrosurgery handpiece/pencil with smoke evacuation capability or an electrosurgery handpiece/pencil without smoke evacuation capability. Both the ultrapolar electrosurgery blade of the present invention and the ultrapolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. In instances where tissue cutting and coagulation are performed at the same time without switching between modes or methods, operating time is decreased and the lateral damage to the tissue is reduced or eliminated. Further, use of monopolar energy in a bipolar mode with the ultrapolar electrosurgery blade of the present invention and the ultrapolar electrosurgery blade assembly with argon beam capability of the present invention essentially eliminates the risk of current diversion that can occur in monopolar systems. In addition, performing both tissue cutting and coagulation at the same time along with smoke evacuation will protect the surgeon and staff from inhaling smoke and particles. It will also enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to an ultrapolar electrosurgery blade which uses monopolar energy in a bipolar mode and which includes a) top and bottom thin elongated conductive members in vertical alignment with one another and spaced apart from one another along their lengths where each of the top and bottom thin elongated conductive members includes opposing planar sides, a sharp cutting end for cutting, and an opposite non-cutting end, b) a non-conductive coating covering both opposing planar sides of the top and bottom thin elongated conductive members and the space located between them to create opposing non-conductive sides of the ultrapolar electrosurgery blade where the cutting ends of the thin elongated conductive members and their opposite non-cutting ends remain exposed, and c) both return and active conductive contact layers positioned on each of the opposing non-conductive sides of the ultrapolar electrosurgery blade. During use, one of the top and bottom thin elongated conductive members functions as an active electrode while the other thin elongated conductive member functions as a return electrode. Further, the return conductive contact layers located on both opposing non-conductive sides of the ultrapolar electrosurgery blade may be in communication with the non-cutting end of the thin elongated conductive member that functions as a return electrode and the active conductive contact layers located on both opposing non-conductive sides of the ultrapolar electrosurgery blade may be in communication with the non-cutting end of the thin elongated conductive member that functions as an active electrode. In addition, the return conductive contact layers on the opposing non-conductive sides of the ultrapolar electrosurgery blade may be connected to one another by extending the return conductive contact layers over a top or bottom of the ultrapolar electrosurgery blade and the active conductive contact layers on the opposing non-conductive sides of the ultrapolar electrosurgery blade may be connected to one another by extending the active conductive contact layers over a top or bottom of the ultrapolar electrosurgery blade.

The ultrapolar electrosurgery blade may further include a non-conductive support member/socket having two openings therein positioned in vertical alignment with one another wherein a portion of each of the top and bottom thin elongated conductive members located near their non-cutting ends are respectively contained within one of the two openings of the support member/socket so that the ultrapolar electrosurgery blade of the present invention can be seated within, and connected to, an electrosurgery pencil. The non-conductive support member may have different configurations and shapes depending on whether the ultrapolar electrosurgery blade is used in a telescopic or non-telescopic electrosurgery pencil.

The top and bottom thin elongated conductive members may be formed from a single thin conductive member having vertically aligned top and bottom elongated conductive members spaced apart from one another along their lengths with each having a separate sharp cutting end at one end and a non-cutting end at their opposite ends where their non-cutting ends are joined. The non-conductive coating may then be applied to the single thin conductive member (which includes the top and bottom elongated conductive members and the space located between the top and bottom elongated conductive members) to form an electrosurgery blade where at least a portion of the cutting ends of the top and bottom elongated conductive members and their joined opposing non-cutting ends remain exposed and not covered by the non-conductive coating. The joined non-cutting ends of the top and bottom elongated conductive members can then be removed to produce separately exposed and unconnected non-cutting ends for the top and bottom elongated conductive members which can be respectively inserted into a non-conductive support member/socket having two openings (as described above).

One advantage in forming the ultrapolar electrosurgery blade of the present invention using a single thin conductive member having vertically aligned top and bottom elongated conductive members spaced apart from one another along their lengths with separate sharp cutting ends at one end and joined opposite non-cutting ends where the joined ends are later removed to produce separate non-cutting ends is that it facilitates the construction and production of the ultrapolar electrosurgery blade by providing a unitary component for creating separate elements of the blade thereby increasing the consistency and accuracy of the blades. Another advantage of this type of formation of the ultrapolar electrosurgery blades are the increased efficiencies in the production of the blades and the reduction in production costs. Still another advantage of this type of blade formation for the ultrapolar electrosurgery blade of the present invention is that it enhances the strength of the blade as well as the proper functioning of the blade.

In one exemplary embodiment of the ultrapolar electrosurgery blade of the present invention, the non-conductive coating covers at least a portion of the top of the top thin elongated conductive member and at least a portion of the bottom of the bottom thin elongated conductive member. The non-conductive coating may be a continuous coating that also fills in any space located between the sharp cutting ends of the top and bottom thin elongated conductive members. In another exemplary embodiment of the ultrapolar electrosurgery blade of the present invention, a portion of the top of the top thin elongated conductive member is exposed between portions of the non-conductive coating located on the top of the electrosurgery blade and a portion of the bottom of the bottom thin elongated conductive member is exposed between portions of the non-conductive coating located on the bottom of the electrosurgery blade. The ultrapolar electrosurgery blade of the present invention may have a sharp cutting edge that is comprised of the sharp cutting ends of the top and bottom thin elongated conductive members separated by a sharp non-cutting end comprised of the non-conductive coating.

The top and bottom thin elongated conductive members (as well as the single thin conductive member that the top and bottom elongated members may be formed from) may comprise a hard metal such as, for example, stainless steel, titanium, and/or tungsten. The non-conductive coating of the ultrapolar electrosurgery blade of the present invention and the non-conductive support member may be comprised of a ceramic material. The return and active contact layers are conductive layers and may comprise stainless steel, copper, and/or tungsten.

The ultrapolar electrosurgery blade of the present invention which uses monopolar energy in a bipolar mode has sharp cutting edges made of a hard conductive material, such as stainless steel, tungsten, etc. that are separated by a sharp non-conductive cutting edge that can all be used for precisely cutting tissue without the use of any RF energy. However, RF energy can also be used with the ultrapolar electrosurgery blade of the present invention for performing tissue coagulation and/or for enhancing tissue cutting using the ultrapolar electrosurgery blade. When low voltage is used to supply power to the ultrapolar electrosurgery blade of the present invention for coagulation, the sharp cutting edges of the ultrapolar electrosurgery blade can simultaneously be used for cutting without the need to provide higher voltage to the ultrapolar electrosurgery blade to carry out the cutting. Therefore, there is no need to switch over to a cutting mode to perform cutting and instead both cutting and coagulation can be performed simultaneously at low power levels supplied from the generator.

Only very low power is required to employ the ultrapolar electrosurgery blade of the present invention for both cutting and coagulation thus substantially reducing the damage to a patient's lateral tissue. Cutting is performed using the sharp cutting edge/end of the ultrapolar blade and coagulation can be performed using any of the conductive members or conductive contact layers that comprise part of the blade. For example, low power can be supplied to the ultrapolar electrosurgery blade of the present invention and the exposed sharp conductive cutting ends of the elongated conductive members covered by the non-conductive coating can be used to coagulate tissue. In another example, low power can be supplied to the ultrapolar electrosurgery blade of the present invention and tissue coagulation can be performed by tilting the ultrapolar electrosurgery blade of the present invention on its side so that active and return conductive layers located on the non-conductive coating of the ultrapolar electrosurgery blade come into contact with the patient's tissue to seal small vessels and stop the bleeding. Further, since the ultrapolar electrosurgery blade of the present invention includes active and return conductive members/electrodes that are both attached to the generator, only a very small amount of a patient's tissue located between the electrodes or adjacent to the electrodes is included in the circuit thereby eliminating the risk of current diversion to other parts of the patient that can occur in monopolar systems where the entire patient is in the circuit.

The present invention is also directed to an ultrapolar electrosurgery blade assembly having argon beam capability. The ultrapolar electrosurgery blade assembly of the present invention includes the ultrapolar electrosurgery blade described above and further includes a non-conductive tube member having a hollow tubular shaped opening contained therein and a slot where the slot is positioned over the top of the ultrapolar electrosurgery blade, and a conductive hollow tubular member contained within at least a portion of the non-conductive tube member. In one exemplary embodiment of the ultrapolar electrosurgery blade assembly of the present invention, a portion of the top of the top thin elongated conductive member is exposed between portions of the non-conductive coating located on the top of the ultrapolar electrosurgery blade and contained within the non-conductive tube member and the ultrapolar electrosurgery blade assembly further includes a conductive projection extending from the conductive hollow tubular member contained within the non-conductive tube member. In another exemplary embodiment of the ultrapolar electrosurgery blade assembly of the present invention, the non-conductive coating covers the top of the top thin elongated conductive member located between the conductive hollow tubular member and the exposed cutting end of the top thin elongated conductive member and the ultrapolar electrosurgery blade assembly further includes a conductive projection extending from an end of the conductive hollow tubular member contained within the non-conductive tube member.

The conductive hollow tubular member contained within the non-conductive tube member may include a slot that, like the slot in the non-conductive tube member, is also positioned over at least a portion of the top of the ultrapolar electrosurgery blade. Like the top and bottom thin elongated conductive members of the ultrapolar electrosurgery blade, the conductive hollow tubular member, as well as the conductive projections, may comprise a hard metal such as, for example, stainless steel, titanium, and/or tungsten. Further, like the non-conductive coating of the ultrapolar electrosurgery blade, the non-conductive tube member may be comprised of a ceramic material.

The ultrapolar electrosurgery blade assembly with argon beam capability of the present invention is capable of coagulating a patient's tissue using argon plasma alone without contacting the patient's tissue (i.e. non-contact argon beam coagulation). In this embodiment of the ultrapolar electrosurgery blade assembly, an exposed portion of the return electrode of the ultrapolar electrosurgery blade is positioned near the top of the electrosurgery blade such that it is in alignment with the conductive hollow tubular member through which the argon gas is introduced and the conductive projection extending from an end of the conductive tube member so that a complete circuit is formed to ionize the argon gas for argon plasma coagulation. The ultrapolar electrosurgery blade assembly of the present invention is also capable of cutting a patient's tissue using the sharp cutting edge (comprising both conductive and non-conductive materials) of the ultrapolar blade alone without any use of RF energy and without any use of argon plasma. The ultrapolar electrosurgery blade assembly of the present invention can also enhance the cutting of a patient's tissue using the sharp conductive cutting edges of the ultrapolar blade by also supplying RF energy to the ultrapolar electrosurgery blade. Moreover, the ultrapolar electrosurgery blade assembly of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar blade can be used without any RF energy for cutting while the conductive tube through which the argon gas is introduced, and which is contained within the non-conductive tube, is activated and directed to provide ionized argon gas for argon plasma coagulation of tissue. In another example, low power may be applied to the ultrapolar blade to coagulate tissue or enhance cutting of tissue while the conductive tube through which the argon gas is introduced, and which is contained within the non-conductive tube, is activated and directed to provide ionized argon gas for argon plasma coagulation of tissue.

Both the ultrapolar electrosurgery blade of the present invention and the ultrapolar electrosurgery blade assembly having argon beam capability of the present invention could be used with an electrosurgery handpiece/pencil with smoke evacuation capability or an electrosurgery handpiece/pencil without smoke evacuation capability. Both the ultrapolar electrosurgery blade of the present invention and the ultrapolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. In instances where tissue cutting and coagulation are performed at the same time without switching between modes or methods, operating time is decreased and the lateral damage to the tissue is reduced or eliminated. Further, use of monopolar energy in a bipolar mode with the ultrapolar electrosurgery blade of the present invention and the ultrapolar electrosurgery blade assembly with argon beam capability of the present invention essentially eliminates the risk of current diversion that can occur in monopolar systems. In addition, performing both tissue cutting and coagulation at the same time along with smoke evacuation will protect the surgeon and staff from inhaling smoke and particles. It will also enable the surgeon or user to more clearly view the surgical site to ensure accuracy during the procedure without the need to stop and switch modes in order to stop bleeding at the surgery site before being able to clearly see the surgical site.

BRIEF DESCRIPTION OF THE DRAWINGS

FIG. 3 represents what the ultrapolar electrosurgery blade of the present invention looks like at a middle stage in the process of making the ultrapolar electrosurgery blade and shows the exemplary embodiment of the thin conductive member of FIG. 1 coated with a non-conductive coating except for the cutting ends and the joined non-cutting ends of the top and bottom elongated conductive members where the non-conductive coating is represented by light shade hash marks and/or hash marks made of unconnected dots;

FIG. 4 is a front end view of a support member/socket/connector member which retains a portion of the unconnected non-cutting ends of the top and bottom elongated conductive members of the ultrapolar electrosurgery blade of the present invention thereby facilitating the connection of the ultrapolar electrosurgery blade of the present invention to an electrosurgery pencil.

FIG. 5 is a top view of the incomplete middle stage blade of the ultrapolar electrosurgery blade of the present invention shown in FIG. 3 with the thin conductive member shown in phantom;

FIG. 6 is a bottom view of the incomplete middle stage blade of the ultrapolar electrosurgery blade of the present invention shown in FIG. 3 with the thin conductive member shown in phantom;

FIG. 7 is an external side view showing the incomplete middle stage blade of the ultrapolar electrosurgery blade shown in FIG. 3 with the joined portion of the non-cutting ends of the top and bottom elongated conductive members removed and the top and bottom elongated conductive members covered by the non-conductive coating shown in phantom;

FIG. 8 is a top view of the incomplete middle stage blade of the ultrapolar electrosurgery blade of the present invention shown in FIG. 7 with the top elongated conductive member covered by the non-conductive coating shown in phantom;

FIG. 9 is a bottom view of the incomplete middle stage blade of the ultrapolar electrosurgery blade of the present invention shown in FIG. 7 with the bottom elongated conductive member covered by the non-conductive coating shown in phantom;

FIG. 10 is a front end view of an exemplary embodiment of a support member/connector member into which unconnected non-cutting ends of the top and bottom elongated conductive members of the ultrapolar electrosurgery blade are placed so that the ultrapolar electrosurgery blade of the present invention can be connected to, and unconnected or removed from, an electrosurgery pencil;

FIG. 11 is an end view of the support member/connector member shown in FIG. 10 showing conductive unconnected non-cutting ends of the ultrapolar electrosurgery blade of the present invention retained within the openings in the support member/connector member;

FIG. 12 is a partial top view of another incomplete middle stage blade embodiment of the ultrapolar electrosurgery blade of the present invention showing a sharp cutting end beveled on both sides to create a sharp cutting tip;

FIGS. 13-14 are opposing external side views showing an exemplary embodiment of the ultrapolar electrosurgery blade of the present invention made from the incomplete middle stage blade embodiments shown in FIGS. 3 and 5-9;

FIG. 15 is a top view of the exemplary embodiment of the ultrapolar electrosurgery blade of the present invention shown in FIG. 13;

FIG. 16 is a bottom view of the exemplary embodiment of the ultrapolar electrosurgery blade of the present invention shown in FIG. 13;

FIG. 17 is a partial perspective view of the exemplary embodiment of the ultrapolar electrosurgery blade of the present invention shown in FIGS. 13-16;

FIGS. 18 and 19 are opposing perspective side views of the exemplary embodiment of the ultrapolar electrosurgery blade of the present invention shown in FIGS. 13-16 to further reveal the shape of the ultrapolar electrosurgery blade of the present invention;

FIG. 25 is a side perspective view of another exemplary embodiment of the ultrapolar electrosurgery blade assembly of the present invention having argon beam capability for providing argon plasma assisted coagulation with the return electrode extending along part of the bottom of the ultrapolar blade; and FIG. 26 is a side perspective view of still another exemplary embodiment of the ultrapolar electrosurgery blade assembly of the present invention having argon beam capability which is capable of providing both argon plasma coagulation and argon plasma assisted coagulation.

DETAILED DESCRIPTION OF EXEMPLARY EMBODIMENTS

Figure 1:
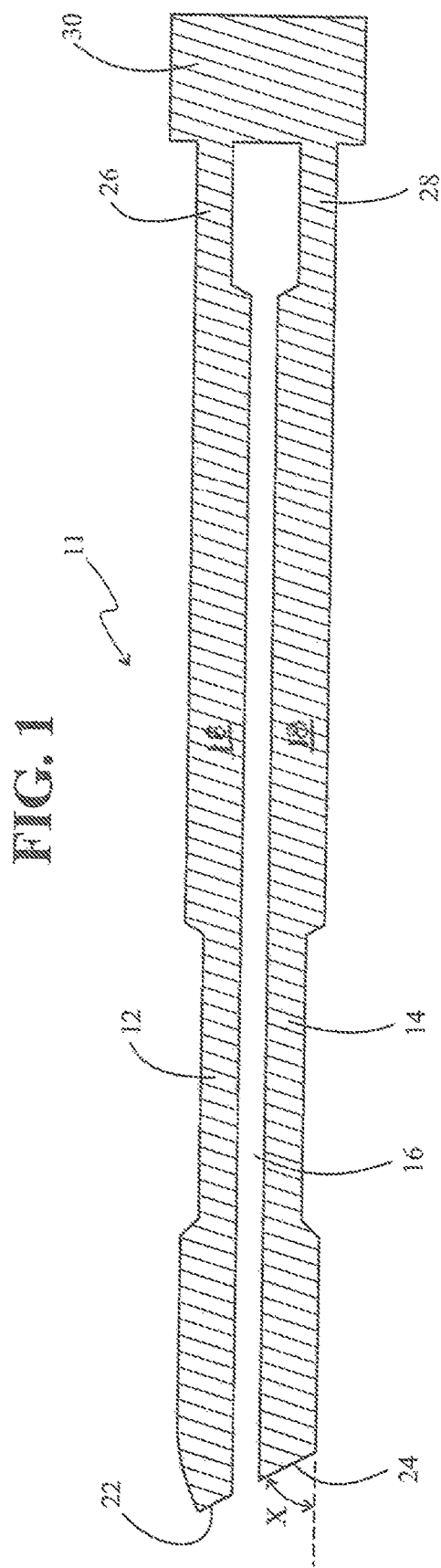
FIG. 1 is a side view of an exemplary embodiment of the thin conductive member having top and bottom thin elongated conductive members used to make the ultrapolar electrosurgery blade of the present invention.

The exemplary embodiments of the ultrapolar electrosurgery blade and ultrapolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. The ultrapolar electrosurgery blade of the present invention is capable of cutting tissue with the sharp conductive cutting ends of the blade without using RF energy as well as cutting tissue with the sharp non-conductive cutting end/edge that is located between the sharp conductive cutting ends. In addition, the ultrapolar electrosurgery blade of the present invention is capable of coagulating tissue and/or enhanced cutting of tissue by supplying very low power, such as 5 to 15 watts, to the ultrapolar electrosurgery blade, and simultaneously cutting and coagulating tissue by cutting tissue with the sharp cutting ends of the ultrapolar electrosurgery blade while coagulating tissue by applying very low power to the ultrapolar electrosurgery blade.

The ultrapolar electrosurgery blade assembly of the present invention with a sharp cutting edge and argon beam capability enables a user or surgeon to perform cutting and coagulation without the need to switch between cutting and coagulation modes. It also enables a user or surgeon to choose from a number of different separate or combined tissue cutting and coagulation methods since different methods may work best depending on the surgical procedure and circumstances that present themselves during surgery. The ultrapolar electrosurgery blade assembly with argon beam capability of the present invention is capable of coagulating a patient's tissue using argon plasma alone without contacting the patient's tissue (i.e. non-contact argon beam coagulation). The ultrapolar electrosurgery blade assembly of the present invention is also capable of cutting a patient's tissue using the sharp cutting edge (comprising both conductive and non-conductive materials) of the ultrapolar blade alone without any use of RF energy and without any use of argon plasma. The ultrapolar electrosurgery blade assembly of the present invention can also enhance the cutting of a patient's tissue using the sharp conductive cutting edges of the ultrapolar blade by also supplying RF energy to the ultrapolar electrosurgery blade.

Further, the ultrapolar electrosurgery blade assembly of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar blade can be used without any RF energy for cutting while the conductive tube through which the argon gas is introduced, and which is contained within the non-conductive tube, is activated and directed to provide ionized argon gas for argon plasma coagulation of tissue. In another example, low power may be applied to the ultrapolar blade to coagulate tissue using the active and return electrodes or the active and return conductive layers or to enhance cutting of tissue using the active and return electrodes while the conductive tube through which the argon gas is introduced, and which is contained within the non-conductive tube, is activated and directed to provide ionized argon gas for argon plasma coagulation of tissue.

The identity of the elements/features that relate to the numbers shown in the drawing figures are as follows:
- 10 incomplete middle stage blade of the ultrapolar electrosurgery blade
- 11 thin conductive member
- 12 top thin elongated conductive member
- 14 bottom thin elongated conductive member
- 16 elongated space between top and bottom thin elongated conductive members
- 18 opposing planar sides (of top and bottom thin elongated conductive members)
- 22 sharp cutting end of top thin elongated conductive member
- 24 sharp cutting end of bottom thin elongated conductive member
- 26 opposite non-cutting end of top thin elongated conductive member
- 28 opposite non-cutting end of bottom thin elongated conductive member
- 30 portion of thin conductive member joining opposite non-cutting ends of top and bottom thin elongated conductive members 26 and 28
- 31 thin conductive member
- 32 top thin elongated conductive member
- 34 bottom thin elongated conductive member
- 36 elongated space between top and bottom thin elongated conductive members
- 38 opposing planar sides (of top and bottom thin elongated conductive members)
- 42 sharp cutting end of top thin elongated conductive member
- 44 sharp cutting end of bottom thin elongated conductive member
- 46 opposite non-cutting end of top thin elongated conductive member
- 48 opposite non-cutting end of bottom thin elongated conductive member
- 50 portion of thin conductive member joining opposite non-cutting ends of top and bottom thin elongated conductive members 46 and 48
- 60 non-conductive coating/housing
- 62 non-conductive support member/socket/connecting member
- 63 rounded top portion (of non-conductive support member/socket/connecting member)
- 65 rounded bottom portion (of non-conductive support member/socket/connecting member)
- 64 two vertically aligned openings
- 66 top of the top thin elongated conductive member
- 68 bottom of the bottom thin elongated conductive member
- 70 sharp non-conductive cutting end
- 72 non-conductive support member/socket/connecting member for ultrapolar telescopic electrosurgery pencil
- 73 rounded top portion (of non-conductive support member/socket/connecting member for ultrapolar telescopic electrosurgery pencil)
- 74 two vertically aligned openings
- 80 ultrapolar electrosurgery blade of the present invention
- 82 opposing non-conductive sides (of the ultrapolar electrosurgery blade 80)
- 84 return conductive layers 86 active conductive layers
100 ultrapolar electrosurgery blade assembly
120 non-conductive tube member
122 hollow tubular shaped opening (of non-conductive tube member)
124 slot (of non-conductive tube member)
130 conductive hollow tubular member
132 conductive projection
200 ultrapolar electrosurgery blade assembly
220 non-conductive tube member
222 hollow tubular shaped opening (of non-conductive tube member)
224 slot (of non-conductive tube member)
230 conductive hollow tubular member
232 conductive projection
300 ultrapolar electrosurgery blade assembly
320 non-conductive tube member
322 hollow tubular shaped opening (of non-conductive tube member)
324 slot (of non-conductive tube member)
330 conductive hollow tubular member
332 conductive projection
334 slot (of conductive hollow tubular member)

FIG. 1 is a side view of an exemplary embodiment of a thin conductive member 11 having top and bottom thin elongated conductive members 12, 14 used to make the ultrapolar electrosurgery blade 10 of the present invention. Thin conductive member 11 includes a top thin elongated conductive member 12 and a bottom thin elongated conductive member 14 in vertical alignment with one another and separated from one another along their lengths by a space 16. The top and bottom elongated conductive members 12, 14 each have opposing planar sides 18, a sharp cutting end 22, 24 and an opposite non-cutting end 26, 28 where the opposite non-cutting ends 26, 28 are joined by a portion 30 of the thin conductive member 11. In one exemplary embodiment of the thin conductive member 11, the sharp cutting ends 22, 24 of the thin conductive member 11 form an angle X relative to a plane that is in horizontal alignment with the bottom of the bottom thin elongated conductive member 14 where X is a sixty degree angle.

Figure 2:
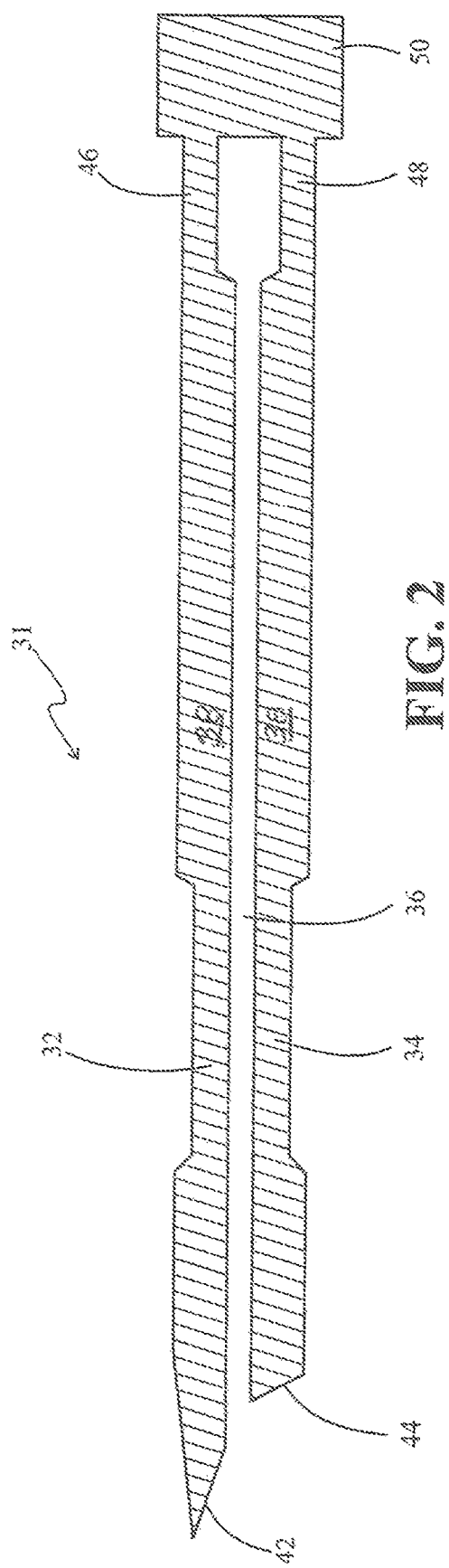
FIG. 2 is a side view of another exemplary embodiment of the thin conductive member having top and bottom thin elongated conductive members used to make the ultrapolar electrosurgery blade of the present invention.

A side view of another exemplary embodiment of a thin conductive member 31 having top and bottom thin elongated conductive members 32, 34 used to make the ultrapolar electrosurgery blade 10 of the present invention is shown in FIG. 2. Like the thin conductive member 11 shown in FIG. 1, thin conductive member 31 includes a top thin elongated conductive member 32 and a bottom thin elongated conductive member 34 in vertical alignment with one another and separated from one another along their lengths by a space 36. The top and bottom elongated conductive members 32, 34 each have opposing planar sides 38, a sharp cutting end 42, 44 and an opposite non-cutting end 46, 48 where the opposite non-cutting ends 46, 48 are joined by a portion 50 of the thin conductive member 31. As shown in FIG. 2, the sharp cutting end 42 of top thin elongated conductive member 32 extends well beyond the sharp cutting end 44 of the bottom thin elongated conductive member 34 and the angle of the sharp cutting end 44 in relation to the bottom of the bottom thin elongated conductive member 34 is much steeper than the angle of the sharp cutting end 42 in relation to the bottom of the top thin elongated conductive member 32. It will be understood by those skilled in the art that the sharp cutting ends of the top and bottom thin elongated conductive members of the ultrapolar electrosurgery blade may include any number of shapes and/or configurations depending on the type and circumstances of the surgical procedure to be performed using the ultrapolar electrosurgery blade.

FIG. 3 represents what the ultrapolar electrosurgery blade of the present invention looks like at a middle stage in the process of making the ultrapolar electrosurgery blade and shows the exemplary embodiment of the thin conductive member 11 of FIG. 1 coated with a non-conductive coating 60 except for the cutting ends 22, 24 and the joined non-cutting ends 26, 28, 30 of the top and bottom elongated conductive members 12, 14 where the non-conductive coating 60 is represented by light shade hash marks and/or hash marks made of unconnected dots. FIG. 5 is a top view of the incomplete middle stage blade 10 of the ultrapolar electrosurgery blade of the present invention shown in FIG. 3 with the thin conductive member 11 shown in phantom and FIG. 6 is a bottom view of the incomplete middle stage blade 10 of the ultrapolar electrosurgery blade of the present invention shown in FIG. 3 with the thin conductive member 11 shown in phantom. As can be seen from FIGS. 3 and 5-6, the non-conductive coating 60 covers the thin conductive member 11 except for sharp cutting ends 22, 24 of the top and bottom elongate conductive members 12, 14, a portion of the top 66 of the of the top elongated conductive member 12, a portion of the bottom 68 of the bottom elongated conductive member 14, the non-cutting ends 26, 28 of the top and bottom elongated conductive members 12, 14 and the portion 30 of the thin conductive member 11 that joins the non-cutting ends 26, 28.

After the non-conductive coating 60 is applied to the thin conductive member 11 and the coating 60 is set, the portion 30 that joins the non-cutting ends 26, 28 is removed as shown in FIG. 7 to provide a middle stage ultrapolar electrosurgery blade 10 having unconnected conductive non-cutting ends 26, 28 supported by a support member/socket/connecting member 62 which facilitates connection of the ultrapolar electrosurgery blade of the present invention to an electrosurgery pencil. FIG. 7 is an external side view showing the incomplete middle stage blade 10 of the ultrapolar electrosurgery blade shown in FIG. 3 with the joined portion 30 of the non-cutting ends 26, 28 of the top and bottom elongated conductive members 12, 14 removed and most of the top and bottom elongated conductive members 12, 14 covered by the non-conductive coating 60 shown in phantom. Advantages in forming the ultrapolar electrosurgery blade of the present invention using a single thin conductive member 11 having vertically aligned top and bottom elongated conductive members 12, 14 spaced apart from one another along their lengths with separate sharp cutting ends 22, 24 at one end and joined opposite non-cutting ends 26, 28, 30 where the joined ends are later removed to produce separate non-cutting ends 26, 28 include 1) facilitation of the construction and production of the ultrapolar electrosurgery blade of the present invention by providing a unitary component for creating separate elements of the blade thereby increasing the consistency and accuracy of the blades, 2) increased efficiencies in the production of the blades and the reduction in production costs, and 3) enhanced strength of the blade as well as the enhanced proper functioning of the blade.

FIG. 8 is a top view of the incomplete middle stage blade 10 of the ultrapolar electrosurgery blade of the present invention shown in FIG. 7 with the top elongated conductive member 12 covered by the non-conductive coating 60 shown in phantom. A portion of the top 66 of the top elongated conductive member 12 is exposed between portions of non-conductive coating 60 located on a top of the ultrapolar electrosurgery blade. FIG. 9 is a bottom view of the incomplete middle stage blade 10 of the ultrapolar electrosurgery blade of the present invention shown in FIG. 7 with the bottom elongated conductive member 14 covered by the non-conductive coating 60 shown in phantom. A portion of the bottom 68 of the bottom elongated conductive member 14 is exposed between portions of non-conductive coating 60 located on a bottom of the ultrapolar electrosurgery blade.

Further, as shown in FIG. 7, the non-conductive coating is a continuous coating that fills elongated space 16 located between the top and bottom elongated conductive members 12, 14 as well as any space located between the sharp cutting ends 22, 24 of the top and bottom elongated conductive members 12, 14. The space between the sharp cutting ends 22, 24 of the top and bottom elongated conductive members 12, 14 that is filled with the non-conductive coating 60 forms a sharp non-conductive cutting end 70 positioned between the sharp conductive cutting ends 22, 24 of the ultrapolar electrosurgery blade.

FIG. 10 is a front end view of an exemplary embodiment of a support member/socket/connector member 62 into which unconnected non-cutting ends 26, 28 of the top and bottom elongated conductive members 12, 14 of the ultrapolar electrosurgery blade are placed so that the ultrapolar electrosurgery blade of the present invention can be easily connected to, and unconnected or removed from, an electrosurgery pencil. The support member/socket/connector member 62 includes two vertically aligned openings 64 so that conductive non-cutting ends 26, 28 can be respectively retained in them. An end view of the support member/connector member 62 shown in FIG. 10 showing conductive unconnected non-cutting ends 26, 28 of the ultrapolar electrosurgery blade of the present invention retained within the openings 64 in the support member/socket/connector member 62 is shown in FIG. 11.

A partial top view of another incomplete middle stage blade embodiment 10 of the ultrapolar electrosurgery blade of the present invention showing a sharp cutting end beveled on both sides to create a sharp cutting tip 22 is shown in FIG. 12.

FIGS. 13-14 are opposing external side views showing an exemplary embodiment of the ultrapolar electrosurgery blade 80 of the present invention made from the incomplete middle stage blade embodiments 10 shown in FIGS. 3 and 5-9. The non-conductive coating 60 covers both opposing planar sides of the top and bottom thin elongated conductive members and the space located between them (as shown in FIGS. 3 and 7) to create opposing non-conductive sides 82 of the ultrapolar electrosurgery blade 80 where the cutting ends 22, 24 of the thin elongated conductive members (not shown as they are covered with non-conductive coating 60) and their opposite non-cutting ends 26, 28 remain exposed. Both return and active conductive layers 84, 86 are positioned on each of the opposing non-conductive sides 82 of the ultrapolar electrosurgery blade 80. During use, one of the top and bottom thin elongated conductive members functions as an active electrode (see 22) while the other thin elongated conductive member functions as a return electrode (see 24). Further, the return conductive layers 84 located on both opposing non-conductive sides 82 of the ultrapolar electrosurgery blade 80 may be in communication with the non-cutting end of the thin elongated conductive member that functions as a return electrode (see 28) and the active conductive contact layers 86 located on both opposing non-conductive sides 82 of the ultrapolar electrosurgery blade 80 may be in communication with the non-cutting end of the thin elongated conductive member that functions as an active electrode (see 26).

As shown in FIG. 13, one end of the return conductive layer 84 located on non-conductive side 82 of the ultrapolar electrosurgery blade 80 is located near the cutting end 22 of the thin elongated conductive member that functions as an active electrode. Return conductive layer 84 extends diagonally across the non-conductive side 82 of the blade 80 and the other end of the return conductive layer 84 is in communication with the non-cutting end of the thin elongated conductive member that functions as a return electrode (see 28). The active conductive layer 86 located on conductive side 82 of blade 80 is positioned beneath and in vertical alignment with return conductive layer 84 and one end of the active conductive layer 86 is located near the cutting end 24 of the thin elongated conductive member that functions as a return electrode. The other end of active conductive layer 86 ends near a bottom of the blade 80 near a mid-portion of the blade 80. As shown in FIG. 14, the return and active conductive layers 84, 86 located on the opposite non-conductive side 82 of the blade 80 comprise the exact opposite of the return and active conductive layer configurations that they have in FIG. 13. The path/configuration of the active conductive layer 86 on the opposite non-conductive side 82 not shown in FIG. 13 is shown in phantom while the path/configuration of the return conductive layer 84 on the opposite non-conductive side 82 not shown in FIG. 14 is shown in phantom.

In addition, the return conductive contact layers 84 on the opposing non-conductive sides 82 of the ultrapolar electrosurgery blade 80 may be connected to one another by extending the return conductive contact layers 84 over a top or bottom of the ultrapolar electrosurgery blade 80 and the active conductive contact layers 86 on the opposing non-conductive sides 82 of the ultrapolar electrosurgery blade 80 may be connected to one another by extending the active conductive contact layers 86 over a top or bottom of the ultrapolar electrosurgery blade 80. FIG. 15 is a top view of the exemplary embodiment of the ultrapolar electrosurgery blade 80 of the present invention shown in FIG. 13 and FIG. 16 is a bottom view of the exemplary embodiment of the ultrapolar electrosurgery blade 80 of the present invention shown in FIG. 13. FIGS. 13 and 15 show return conductive layers 84 connected to one another by extending over a top of the ultrapolar electrosurgery blade 80 while FIGS. 14 and 16 show active conductive layers 86 connected to one another by extending over a bottom of the ultrapolar electrosurgery blade 80.

FIG. 17 is a partial perspective view of the exemplary embodiment of the ultrapolar electrosurgery blade 80 of the present invention shown in FIGS. 13-16. FIG. 17 clearly shows sharp conductive cutting ends 22, 24 which function as active and return electrodes, respectively, and sharp non-conductive cutting end 74 comprised of the non-conductive coating 60 located between the sharp conductive cutting ends 22, 24. FIG. 17 also clearly shows a portion of the top 66 of the top elongated conductive member 12 exposed between portions of non-conductive coating 60 located on top of the ultrapolar electrosurgery blade 80 and in communication with the sharp cutting end 22. Both return and active conductive layers 84, 86 are located on each opposing non-conductive side 82 of the ultrapolar electrosurgery blade.

FIGS. 18 and 19 are opposing perspective side views of the exemplary embodiment of the ultrapolar electrosurgery blade 80 of the present invention shown in FIGS. 13-16 to further reveal the shape of the ultrapolar electrosurgery blade of the present invention. The non-conductive coating 60 covers both opposing planar sides of the top and bottom thin elongated conductive members and the space located between them to create opposing non-conductive sides 82 of the ultrapolar electrosurgery blade 80 where the cutting ends 22, 24 of the thin elongated conductive members and their opposite non-cutting ends 26, 28 remain exposed. Both return and active conductive layers 84, 86 are positioned on each of the opposing non-conductive sides 82 of the ultrapolar electrosurgery blade 80. During use, one of the top and bottom thin elongated conductive members functions as an active electrode (see 22) while the other thin elongated conductive member functions as a return electrode (see 24). The return conductive layers 84 located on both opposing non-conductive sides 82 of the ultrapolar electrosurgery blade 80 are in communication with the non-cutting end of the thin elongated conductive member that functions as a return electrode (see 28) and the active conductive layers 86 located on both opposing non-conductive sides 82 of the ultrapolar electrosurgery blade 80 are in communication with the non-cutting end of the thin elongated conductive member that functions as an active electrode (see 26).

Figure 20:
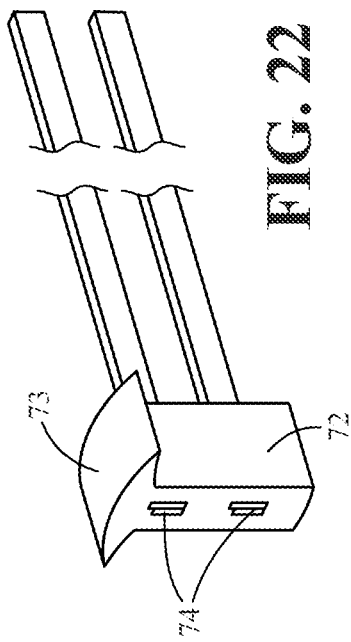
FIGS. 20-21 show different views of an exemplary non-conductive support member/socket/connector member that comprises part of the ultrapolar electrosurgery blade of the present invention when used in a non-telescopic electrosurgery pencil.
Figure 22:
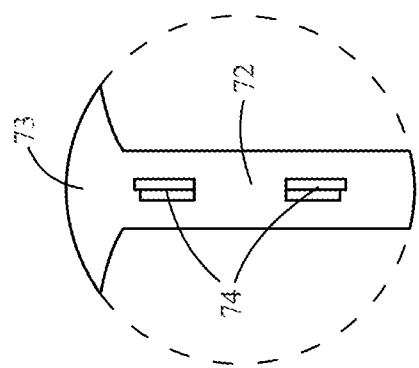
FIGS. 22-23 show different views of an exemplary non-conductive support member/socket/connector member that comprises part of the ultrapolar electrosurgery blade of the present invention when used in a telescopic electrosurgery pencil.
Figure 21:
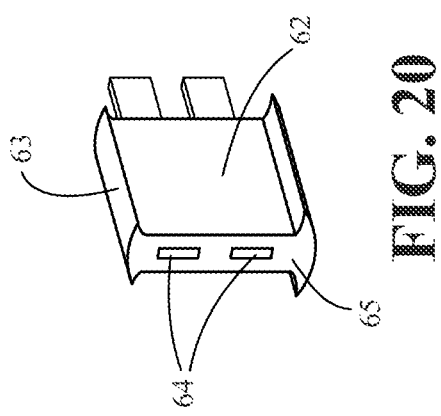
Figure 23:
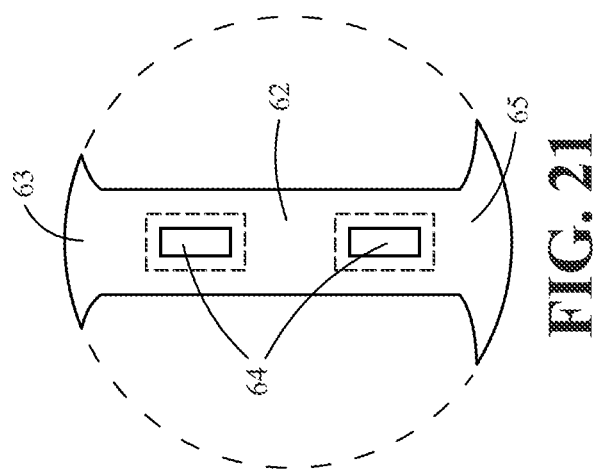

FIGS. 20-21 show different views of an exemplary non-conductive support member/socket/connector member 62 that comprises part of the ultrapolar electrosurgery blade 80 of the present invention when used in a non-telescopic electrosurgery pencil and FIGS. 22-23 show different views of an exemplary embodiment of the non-conductive support member/socket/connector member 72 that comprises part of the ultrapolar electrosurgery blade 80 of the present invention when used in a telescopic electrosurgery pencil. Non-conductive support member/socket/connecting member 62 includes a rounded top portion 63, a rounded bottom portion 65, and two vertically aligned openings 64 for receiving non-cutting ends 26, 28 of top and bottom elongated conductive members 12, 14 and/or portions of the top and bottom elongated conductive members 12, 14 located near the non-cutting ends 26, 28. Non-conductive support member/socket/connecting member 72 includes a rounded top portion 73 and two vertically aligned openings 74 for receiving non-cutting ends 26, 28 of top and bottom elongated conductive members 12, 14 and/or portions of the top and bottom elongated conductive members 12, 14 located near the non-cutting ends 26, 28.

Figure 24:
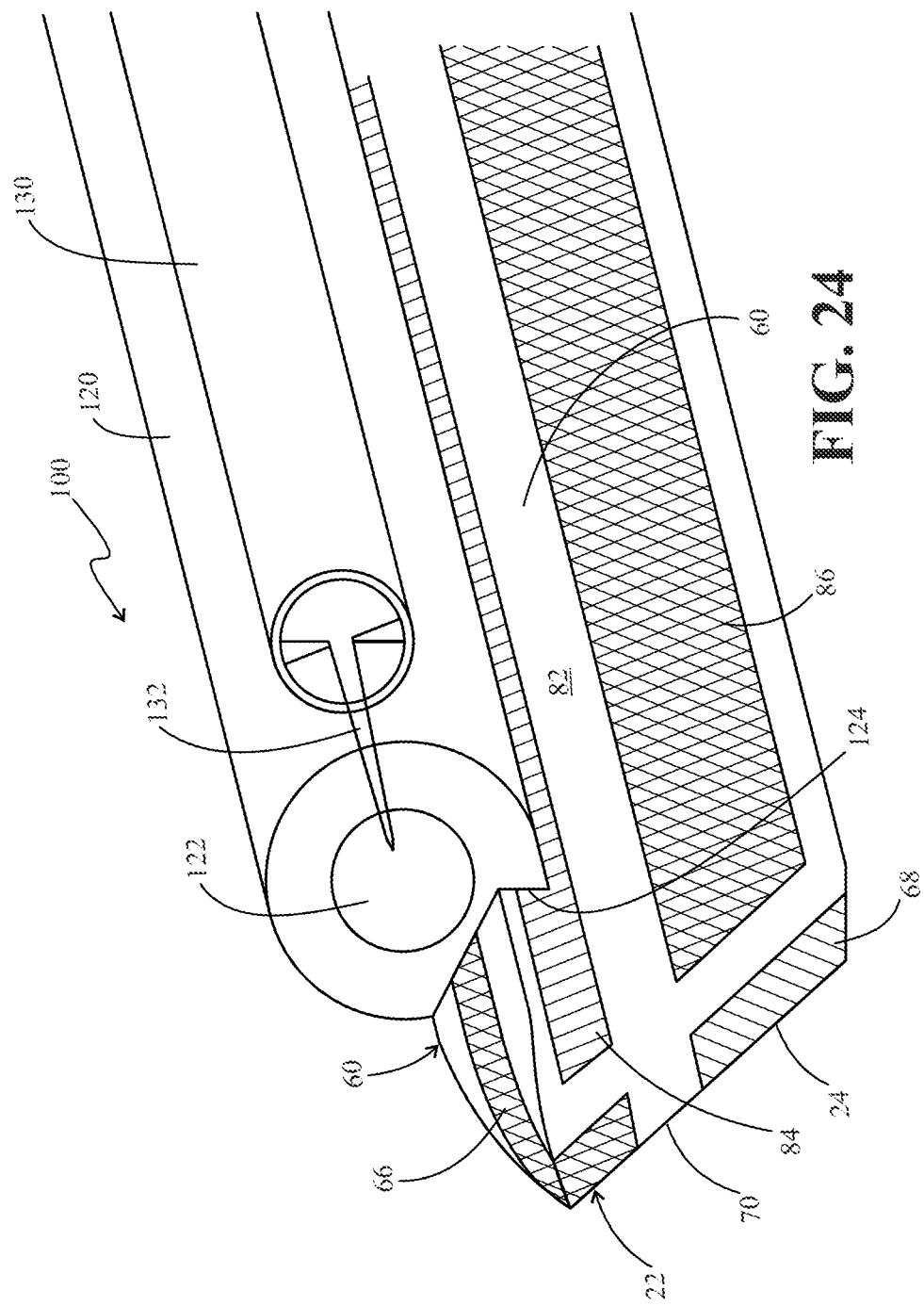
FIG. 24 is a partial perspective view of an exemplary embodiment of the ultrapolar electrosurgery blade assembly of the present invention having argon beam capability for providing argon plasma assisted coagulation.

A partial perspective view of an exemplary embodiment of the ultrapolar electrosurgery blade assembly 100 of the present invention having argon beam capability for providing argon plasma assisted coagulation is shown in FIG. 24. Ultrapolar electrosurgery blade assembly 100 includes the ultrapolar electrosurgery blade 80 previously described above and further includes a non-conductive tube member 120 having a hollow tubular shaped opening 122 contained therein and a slot 124 where the slot is positioned over a top of the ultrapolar electrosurgery blade 80. The ultrapolar electrosurgery blade assembly 100 further includes a conductive hollow tubular member 130 that is contained within at least a portion of the non-conductive tube member 120. Conductive hollow tubular member 130 may also include a conductive projection 132. The sharp cutting edge (comprising conductive cutting ends 22, 24 separated by sharp non-conductive cutting end 70) or a portion of the sharp cutting edge can be used without RF energy for cutting while argon gas is introduced through the conductive hollow tubular member 130 contained within the non-conductive tube member 120 while the conductive hollow tubular member 130 is activated and the conductive projection 132 can direct the ionized argon gas for argon plasma coagulation of tissue. Alternatively, low power may be applied to the ultrapolar electrosurgery blade 80 to coagulate tissue (using conductive cutting edges 22, 24 which act as active and return electrodes or return and active conductive layers 84, 86) or to enhance cutting of tissue (using conductive cutting edges 22, 24 which act as active and return electrodes) while argon gas is introduced through the conductive hollow tubular member 130 contained within the non-conductive tube member 120 while the conductive hollow tubular member 130 is activated and the conductive projection 132 can direct the ionized argon gas for argon plasma coagulation of tissue.

FIG. 25 is a side perspective view of another exemplary embodiment of the ultrapolar electrosurgery blade assembly 200 of the present invention having argon beam capability for providing argon plasma assisted coagulation with the return electrode extending along part of the bottom of the ultrapolar blade 80. Ultrapolar electrosurgery blade assembly 200 includes the ultrapolar electrosurgery blade 80 previously described above and further includes a non-conductive tube member 220 having a hollow tubular shaped opening 222 contained therein and a slot 224 where the slot is positioned over a top of the ultrapolar electrosurgery blade 80. The ultrapolar electrosurgery blade assembly 200 further includes a conductive hollow tubular member 230 that is contained within at least a portion of the non-conductive tube member 220. Conductive hollow tubular member 230 may also include a conductive projection 232. The sharp cutting edge (comprising conductive cutting ends 22, 24 separated by sharp non-conductive cutting end 70) or a portion of the sharp cutting edge can be used without RF energy for cutting while argon gas is introduced through the conductive hollow tubular member 230 contained within the non-conductive tube member 220 while the conductive hollow tubular member 230 is activated and the conductive projection 232 can direct the ionized argon gas for argon plasma coagulation of tissue. Alternatively, low power may be applied to the ultrapolar electrosurgery blade 80 to coagulate tissue (using conductive cutting edges 22, 24 which act as active and return electrodes or using return and active conductive layers 84, 86) or to enhance cutting of tissue (using conductive cutting edges 22, 24 which act as active and return electrodes) while argon gas is introduced through the conductive hollow tubular member 230 contained within the non-conductive tube member 220 while the conductive hollow tubular member 230 is activated and the conductive projection 232 can direct the ionized argon gas for argon plasma coagulation of tissue thereby employing argon plasma assisted cutting and/or coagulation.

FIG. 26 is a side perspective view of still another exemplary embodiment of the ultrapolar electrosurgery blade assembly 300 of the present invention having argon beam capability which is capable of providing both argon plasma coagulation and argon plasma assisted coagulation. Ultrapolar electrosurgery blade assembly 300 includes the ultrapolar electrosurgery blade 80 previously described above and further includes a non-conductive tube member 320 having a hollow tubular shaped opening 322 contained therein and a slot 324 where the slot is positioned over a top of the ultrapolar electrosurgery blade 80. The ultrapolar electrosurgery blade assembly 300 further includes a conductive hollow tubular member 330 that is contained within at least a portion of the non-conductive tube member 320. Conductive hollow tubular member 330 may also include a conductive projection 332. In this embodiment of the ultrapolar electrosurgery blade assembly 300, an exposed portion of the return electrode 22 of the ultrapolar electrosurgery blade 80 is positioned near the top of the electrosurgery blade 80 that is comprised of non-conductive coating 60 such that it is in alignment with the conductive hollow tubular member 330, through which the argon gas is introduced, and the conductive projection 332 extending from an end of the conductive tubular member 332 so that a complete circuit is formed to ionize the argon gas for argon plasma coagulation. The ultrapolar electrosurgery blade assembly 300 of the present invention is also capable of cutting a patient's tissue using the sharp cutting edge (comprising conductive cutting ends 22, 24 separated by sharp non-conductive cutting end 70) of the ultrapolar electrosurgery blade 80 alone without any use of RF energy and without any use of argon plasma. The ultrapolar electrosurgery blade assembly 300 of the present invention can also enhance the cutting of a patient's tissue using the sharp conductive cutting edges 22, 24 of the ultrapolar electrosurgery blade 80 by also supplying RF energy to the exposed portion of the active electrode 24 of the ultrapolar electrosurgery blade 80. Moreover, the ultrapolar electrosurgery blade assembly 300 of the present invention having a sharp cutting edge and argon beam capability enables a user or surgeon to simultaneously perform cutting and coagulation without the need to switch between cutting and coagulation modes by performing argon plasma assisted cutting and coagulation. For example, the sharp cutting edge of the ultrapolar electrosurgery blade 80 can be used without any RF energy for cutting while the conductive hollow tubular member 330 through which the argon gas is introduced, and which is contained within the non-conductive tube member 320, is activated and directed via conductive projection 332 to provide ionized argon gas for argon plasma coagulation of tissue. In another example, low power may be applied to the ultrapolar electrosurgery blade 80 to coagulate tissue (using conductive cutting edges 22, 24 which act as return and active electrodes or using return and active conductive layers 84, 86) or to enhance cutting of tissue (using conductive cutting edges 22, 24 which act as return and active electrodes) while the conductive hollow tubular member 330 through which the argon gas is introduced, and which is contained within the non-conductive tube member 320, is activated and directed via the conductive projection 332 to provide ionized argon gas for argon plasma coagulation of tissue.

The drawings and description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar electrosurgery blade comprising:
   a top thin elongated conductive member and a bottom thin elongated conductive member in vertical alignment with one another and spaced apart from one another along their lengths to form a space between the top and bottom thin elongated conductive members wherein each of the top and bottom thin elongated conductive members includes opposing planar sides, a sharp cutting end and an opposite non-cutting end;
   a non-conductive housing that covers both opposing planar sides of the top and bottom thin elongated conductive members and that fills the space between the top and bottom thin elongated conductive members to create opposing non-conductive sides of the ultrapolar electrosurgery blade wherein at least a portion of the sharp cutting ends of the top and bottom thin elongated conductive members and their opposite non-cutting ends remain exposed; and
   both a return contact layer and an active contact layer positioned on each of the opposing non-conductive sides of the ultrapolar electrosurgery blade wherein an end of the return contact layer is located near an exposed sharp cutting end of the top thin elongated conductive member without touching the exposed sharp cutting end of the top thin elongated conductive member.

2. The ultrapolar electrosurgery blade of claim 1 wherein an end of the active contact layer is located near an exposed sharp cutting end of the bottom thin elongated conductive member without touching the exposed sharp cutting end of the bottom thin elongated conductive member.

3. The ultrapolar electrosurgery blade of claim 1 wherein the return contact layers are in communication with the non-cutting end of one of the top and bottom thin elongated conductive members and the active contact layers are in communication with the non-cutting end of the other of the top and bottom thin elongated conductive members.

4. The ultrapolar electrosurgery blade of claim 1 further comprising a non-conductive support member having two openings therein in vertical alignment with one another wherein a portion of said top and bottom thin elongated conductive members are respectively contained within one of the two openings.

5. The ultrapolar electrosurgery blade of claim 1 wherein the non-conductive housing covers at least a portion of a top of the top thin elongated conductive member and at least a portion of a bottom of the bottom thin elongated conductive member.

6. The ultrapolar electrosurgery blade of claim 1 wherein the non-conductive housing that fills the space located between the sharp cutting ends of the top and bottom thin elongated conductive members forms a non-conductive sharp cutting end located between the sharp cutting ends.

7. The ultrapolar electrosurgery blade of claim 6 wherein at least a portion of a top of the top thin elongated conductive member is exposed between portions of the non-conductive housing located on a top of the electrosurgery blade and at least a portion of a bottom of the bottom thin elongated conductive member is exposed between portions of the non-conductive housing located on a bottom of the electrosurgery blade.

8. The ultrapolar electrosurgery blade of claim 1 wherein the top and bottom thin elongated conductive members comprise a hard metal and the non-conductive housing comprises a ceramic material.

9. An ultrapolar electrosurgery blade assembly that includes the ultrapolar electrosurgery blade of claim 1 and further comprises:
a non-conductive tube member having a hollow tubular shaped opening contained therein and a slot wherein the slot is positioned over a top of the ultrapolar electrosurgery blade; and
a conductive hollow tubular member contained within at least a portion of the non-conductive tube member.

10. The ultrapolar electrosurgery blade assembly of claim 9 further comprising a non-conductive support member having two openings therein in vertical alignment with one another wherein a portion of said top and bottom thin elongated conductive members are respectively contained within one of the two openings.

11. The ultrapolar electrosurgery blade assembly of claim 9 wherein the non-conductive housing that fills the space located between the sharp cutting ends of the top and bottom thin elongated conductive members forms a non-conductive sharp cutting end located between the sharp cutting ends.

12. The ultrapolar electrosurgery blade assembly of claim 9 wherein the return contact layers are in communication with the non-cutting end of one of the top and bottom thin elongated conductive members and the active contact layers are in communication with the non-cutting end of the other of the top and bottom thin elongated conductive members.

13. The ultrapolar electrosurgery blade assembly of claim 9 wherein the top and bottom thin elongated conductive members and the conductive hollow tubular member comprise a hard metal.

14. The ultrapolar electrosurgery blade assembly of claim 9 wherein the non-conductive housing and the non-conductive tube member comprise a ceramic material.

15. An ultrapolar electrosurgery blade comprising:
a top thin elongated conductive member and a bottom thin elongated conductive member in vertical alignment with one another and spaced apart from one another along their lengths wherein each of the top and bottom thin elongated conductive members includes opposing planar sides, a sharp distal-most cutting end and an opposite non-cutting end; and
a non-conductive housing or a non-conductive coating that covers both opposing planar sides of the top and bottom thin elongated conductive members and that fills a space between the top and bottom thin elongated conductive members to create opposing non-conductive sides of the ultrapolar electrosurgery blade wherein at least a portion of the sharp distal-most cutting ends of the top and bottom thin elongated conductive members remain exposed and in a planar relationship with at least a portion of the non-conductive housing or non-conductive coating thereby forming a cutting end of the ultrapolar electrosurgery blade that includes a non-conductive sharp cutting end extending entirely between the sharp distal-most cutting ends of the top and bottom thin elongated conductive members and defining a non-conductive sharp cutting end cutting length, wherein a cutting length of the sharp distal-most cutting ends of the top and bottom thin elongated conductive members is at least as great as the non-conductive sharp cutting end cutting length.

16. The ultrapolar electrosurgery blade of claim 15 further comprising both a return contact layer and an active contact layer positioned on each of the opposing non-conductive sides of the ultrapolar electrosurgery blade.

17. The ultrapolar electrosurgery blade of claim 16 wherein the return contact layers are in communication with the non-cutting end of one of the top and bottom thin elongated conductive members and the active contact layers are in communication with the non-cutting end of the other of the top and bottom thin elongated conductive members.

18. The ultrapolar electrosurgery blade of claim 15 wherein the non-conductive housing or the non-conductive coating covers at least a portion of a top of the top thin elongated conductive member and at least a portion of a bottom of the bottom thin elongated conductive member.

19. The ultrapolar electrosurgery blade of claim 15 wherein at least a portion of a top of the top thin elongated conductive member is exposed between portions of the non-conductive housing or the non-conductive coating located on a top of the electrosurgery blade and at least a portion of a bottom of the bottom thin elongated conductive member is exposed between portions of the non-conductive housing or the non-conductive coating located on a bottom of the electrosurgery blade.

20. An ultrapolar electrosurgery blade assembly that includes the ultrapolar electrosurgery blade of claim 15 and further comprises:
a non-conductive tube member having a hollow tubular shaped opening contained therein and a slot wherein the slot is positioned over a top of the ultrapolar electrosurgery blade; and
a conductive hollow tubular member contained within at least a portion of the non-conductive tube member.

* * * * *